US00PP08033P

United States Patent [19]

Toyama

[11] Patent Number: Plant 8,033

[45] Date of Patent: Nov. 17, 1992

[54] SWEET CHERRY TREE 'PC6659-2'

[75] Inventor: Thomas K. Toyama, Albany, Oreg.

[73] Assignee: Washington State University Research Foundation, Pullman, Wash.

[21] Appl. No.: 664,131

[22] Filed: Mar. 4, 1991

[51] Int. Cl.[5] ..... A01H 5/00

[52] U.S. Cl. ..... Plt./37

[58] Field of Search ..... Plt./37

*Primary Examiner*—James R. Feyrer

*Attorney, Agent, or Firm*—Chernoff, Vilhauer, McClung & Stenzel

[57] ABSTRACT

A new and distinct variety of sweet cherry tree, which bears medium size (average 9 grams in weight), bright, glossy red fruits. Its high quality, attractive fruits ripen about early to mid-Lambert season (5 days after Bing) and are much firmer than Lambert. The tree possesses a broad, spreading habit of growth, being much less upright in growth habit than either Lambert or Bing.

2 Drawing Sheets

BACKGROUND AND SUMMARY OF THE INVENTION

The present invention relates to a new and distinct variety of sweet cherry tree which bears medium size, attractive fruits of excellent quality and flavor.

This new variety was developed at Washington State University Irrigated Agricultural Research and Extension Center (I.A.R.E.C.) at Prosser, Wash. from a cross made in 1966. It was selected in 1977 from several seedlings of the cross Lambert×Van (both unpatented). Second test trees were planted on the Roza unit of the center in the fall of 1974 and came into production in 1980.

The new variety ripens about five (5) days after Bing (unpatented) and trees have been consistently productive, bearing fruits larger and firmer than Bing and much firmer than Lambert (unpatented) with which it is compared to herein. The fruit is Bing shape, glossy and attractive when mature.

Before maturity, the fruit is distinct with a high rib along the suture. Stems are medium length and shorter than those of Lambert. Flesh is medium red, low acid, and possesses good dessert quality.

The tree is vigorous and spreading in habit, and tree size is controlled readily by pruning.

The new variety blooms late, forms flower buds in exceptionally large numbers and is self-sterile but is cross compatible with the Sam and Lambert varieties (both unpatented).

Interest in this new clone is for a very firm shipping variety to replace the much softer fleshed Lambert for the late season fresh market.

Trees of the subject variety are vigorous and compatible on common rootstocks used under sweet cherry trees. The bloom period is late, about in Lambert season and approximately two (2) days after Bing. It is a precocious variety coming into bearing early and bears consistent and abundant crops.

Asexual reproduction of this new and distinct variety, show that its unique and desirable characteristics come true to form and are established and transmitted through succeeding propagations by grafting.

BRIEF DESCRIPTION OF THE DRAWINGS

In the accompanying photographs, vegetative growth, fruit and stones are shown in color as nearly true as is reasonably possible to make in color photographs of this nature.

DETAILED DESCRIPTION

Figure 1:
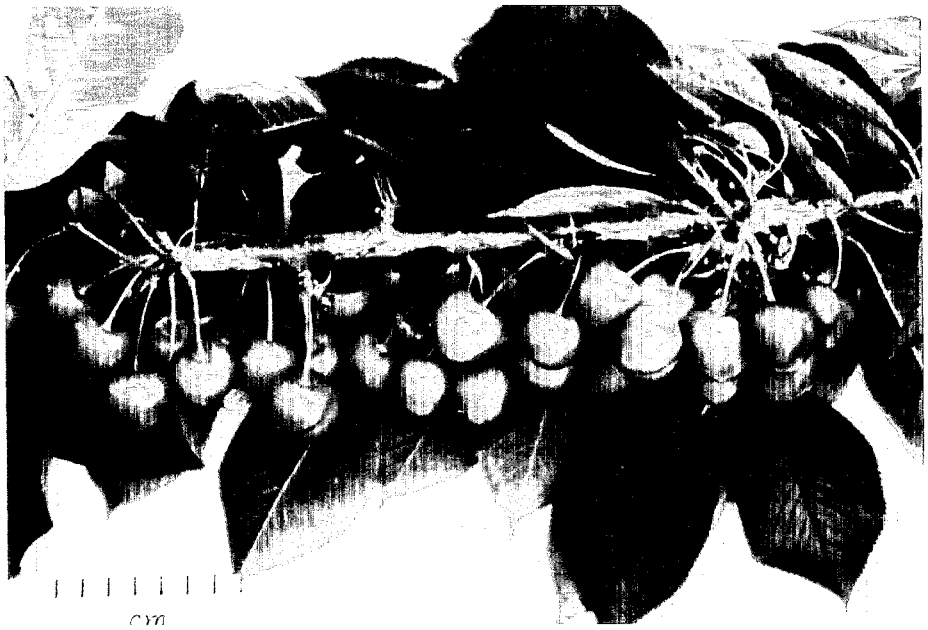
FIG. 1 shows a branch of the subject variety with vegetative growth and fruit.
Figure 2:
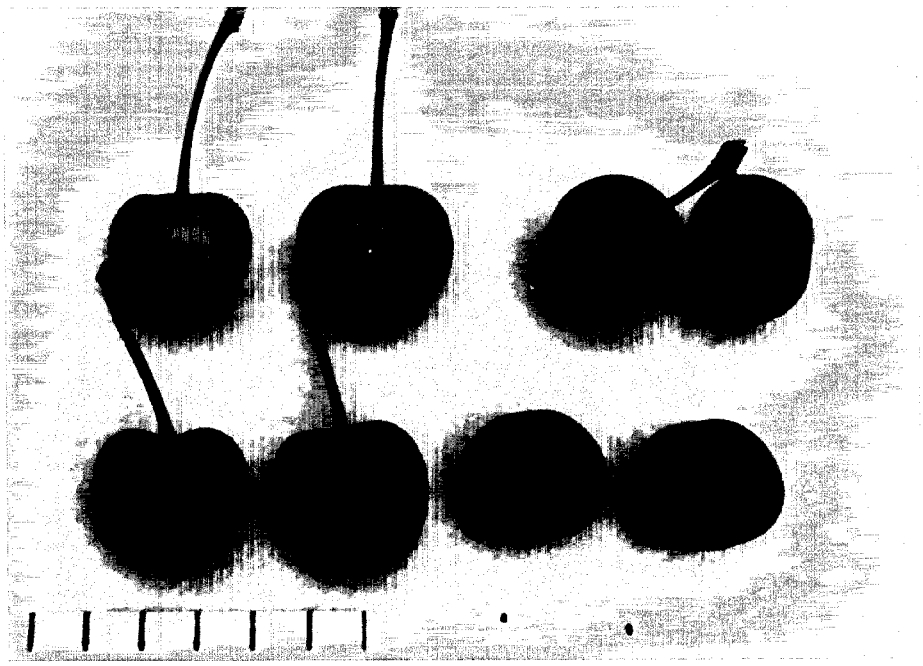
FIG. 2 shows the fruit of the subject variety off of the tree.
Figure 3:
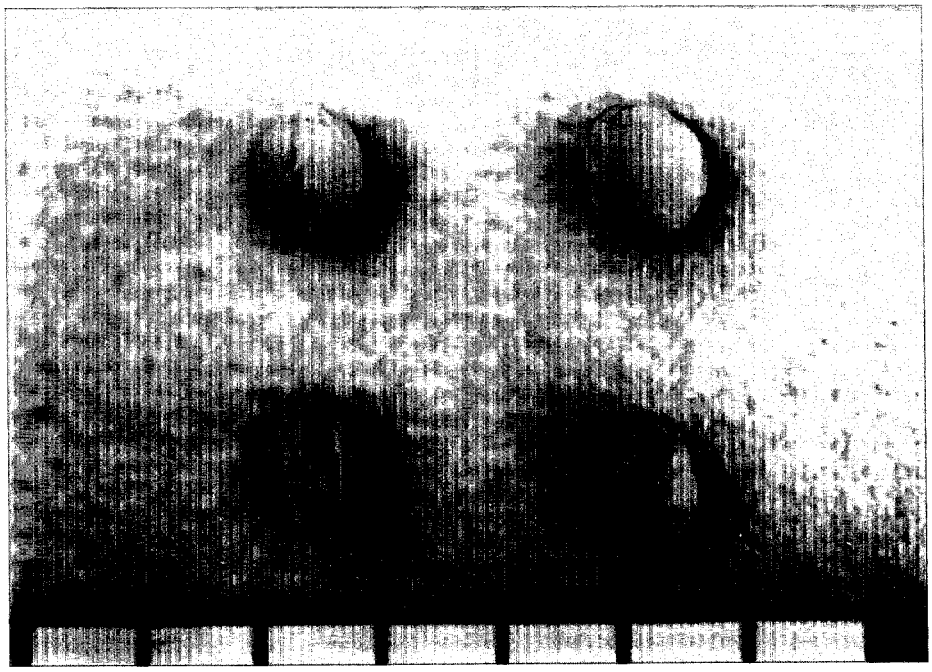
FIG. 3 shows the stones of the subject variety.

Following is a detailed description of the new cherry variety, with color terminology in accordance with the Munsell Color Cascade Chart except where general color terms of ordinary dictionary significance are used.

Trees:

*Size.*—Large.

*Vigor.*—Vigorous.

*Branching habit.*—Spreading.

*Density.*—Average for sweet cherry.

*Form.*—Broadly vase-formed.

*Hardiness.*—Hardy in area where tested — Lower Yakima Valley of Washington.

*Production.*—Very productive.

*Bearing.*—Consistent, regular.

Trunk:

*Size.*—Stocky.

*Bark texture.*—Typical for sweet cherry.

*Bark color.*—Grey-brown (26-13).

*Lenticels.*—Numerous, medium — 3.2 to 5.6 mm in diameter, Green-brown.

Branches:

*Size.*—Stocky.

*Texture.*—Average-typical for sweet cherry.

*Color.*—First year wood, greenish-brown (32-10). Second year wood, grey-brown (24-13).

*Lenticels.*—Numerous, small, 1.5–2.0 mm in diameter, tannish brown.

Leaves: Measurements are from mature leaves attached at midpoint of actively growing upright shoots of current season's growth.

*Size.*—Large 16–18 cm long, 7.5–8.5 cm wide.

*Form.*—Ovate, acuminate, abruptly-acutely pointed.

*Color.*—Upper surface, glossy green (20-13), lower surface-light green (19-10).

*Midvein.*—Medium, light pink (40-8), 1.3 mm in diameter at center of leaf.

*Petiole.*—Long 4.5–5 cm, thick 2.2 mm, light green (19-9) with pink tinge along petiole groove.
*Texture.*—Smooth.
*Margin.*—Crenate to finely serrate.
*Glands.*—Mostly two, variable, positioned both alternate and irregular, medium, mostly reniform shape, shiny with reddish center when immature, darker red (38-13) when mature, glabrous, positioned on rim of petiole groove 3 to 8 mm from base of leaf petiole.
*Stipules.*—Medium, usually two in number, 1.5–2.0 cm in length, light green (18.8).

Flower buds:
*Hardness.*—Hardy.
*Size.*—Medium.
*Length.*—Medium.
*Form.*—Plump, conic, free.

Flowers: Self-sterile.
*Full-bloom.*—April 9 at Prosser test site (5 year avg.) late as compared with other varieties.
*Size.*—Large, 25–30 mm in diameter when fully open.
*Color.*—White.
*Bloom amount.*—Abundant — 5–7 per cluster.
*Petals.*—Average 20 mm in length and 14 mm in width, obovate, cupped slightly inward, white.
*Nectaries.*—Grey-green when mature (22-8).
*Anthers.*—Large, yellow (27-4).
*Pollen.*—Abundant, yellow (27-6).
*Pedicel.*—Medium length 12 to 15 mm, light green (23-7).

Fruit:
*Maturity.*—Eating ripe — June 24 at Prosser test site (1986–1990 five year average.)
*Date of first picking.*—June 24 at Prosser.
*Date of last picking.*—July 3 at Prosser.
*Size.*—Uniform, larger 9.0 grams, diameter transversely across suture — 2.6 to 2.9 cm, diameter apically — 2.2 to 2.4 cm.
*Form.*—Uniform, symmetrical, somewhat heart shaped but with blunt apex end.
*Suture.*—Pronounced ridge, pronounced lip at stem end, very slight darker colored line extends from base to apex.
*Stem cavity.*—Broad, rounded shoulders, medium shallow.
*Base.*—Rounded.
*Apex.*—Slightly rounded to blunt, pistil point apical and distinctive.
*Stem.*—Medium thick, variable, 3.4 to 4.0 cm in length, light green (21-8).

Skin:
*Thickness.*—Medium.

*Texture.*—Medium.
*Tenacity.*—Tenacious to flesh.
*Tendency to crack.*—Susceptible to cracking caused by rain, similar to Bing.
*Down.*—Wanting.
*Color.*—Dark red (38-15).

Flesh:
*Color.*—Red (40-10).
*Surface of pit cavity.*—Dark red (39-12).
*Texture.*—Very firm, crisp.
*Fibers.*—Moderate, cream color, medium coarse.
*Ripens.*—Evenly.
*Flavor.*—Sweet, low acid, fair.
*Juice.*—Red (40-10).
*Aroma.*—None.
*Eating quality.*—Fair.

Stone:
*Type.*—Semi-free.
*Size.*—Medium, 1.0–1.2 cm long, and 1.0 cm wide.
*Form.*—Oval to globose, with protruding wing along basal shoulder of ventral suture.
*Base.*—Rounded.
*Hilium.*—Small, oval to slightly oblong.
*Apex.*—Rounded.
*Sides.*—Equal.
*Surface.*—Irregularly furrowed.
*Ventral edge.*—Narrow suture subtended by two low ridges converging basally and apically.
*Dorsal edge.*—Narrow, smooth, narrow ridge from base to apex.
*Color.*—Tannish white when dry.
*Tendency to split.*—None.

Use:
*Late season shipping.*—Lambert season.

Keeping quality: Good.

Resistance to insects and disease: No particular susceptibility noted.

Shipping quality: Firm; at least as firm as Bing.

Variance in botanical details: The cherry tree and its fruit herein described will vary due to climatic, soil and growing conditions under which the variety may be grown. The present description being of the variety as grown in the Lower Yakima Valley of Washington.

What is claimed is:

1. A new and distinct variety of cherry tree obtained as a seedling of the cross Lambert × Van (both unpatented) is characterized by bearing fruit relatively late in the season that is firmer than that of Lambert, for shipment to the late season fresh market, and by bearing an exceptionally large number of flower buds.

* * * * *